US010674690B2

(12) United States Patent
Tuinstra et al.

(10) Patent No.: US 10,674,690 B2
(45) Date of Patent: Jun. 9, 2020

(54) ACETOLACTATE SYNTHASE HERBICIDE RESISTANT SORGHUM

(71) Applicant: Kansas State University Research Foundation, Manhattan, KS (US)

(72) Inventors: Mitchell R. Tuinstra, West Lafayette, IN (US); Kassim Al-Khatib, Woodland, CA (US)

(73) Assignee: Kansas State University Research Foundation, Manhattan, KS (US)

( * ) Notice: Subject to any disclaimer, the term of this patent is extended or adjusted under 35 U.S.C. 154(b) by 418 days.

(21) Appl. No.: 15/416,521

(22) Filed: Jan. 26, 2017

(65) Prior Publication Data

US 2017/0145436 A1 May 25, 2017

Related U.S. Application Data

(63) Continuation of application No. 11/951,629, filed on Dec. 6, 2007, now Pat. No. 10,519,461.

(60) Provisional application No. 60/873,529, filed on Dec. 7, 2006.

(51) Int. Cl.
*A01H 5/10* (2018.01)
*A01H 6/46* (2018.01)

(52) U.S. Cl.
CPC ............. *A01H 6/4666* (2018.05); *A01H 5/10* (2013.01); *C12Y 202/01006* (2013.01)

(58) Field of Classification Search
None
See application file for complete search history.

(56) References Cited

U.S. PATENT DOCUMENTS

| | | | | |
|---|---|---|---|---|
| 5,633,437 | A | * 5/1997 | Bernasconi | C12N 9/88 435/320.1 |
| 5,767,361 | A | 6/1998 | Dietrich | |
| 5,853,973 | A | * 12/1998 | Kakefuda | C12N 9/88 435/4 |
| 6,211,438 | B1 | * 4/2001 | Anderson | A01H 1/00 800/270 |
| 2003/0236208 | A1 | 12/2003 | Kmiec et al. | |

FOREIGN PATENT DOCUMENTS

| | | |
|---|---|---|
| GB | 2326163 A | 12/1998 |
| WO | WO 2006/007273 A2 | 1/2006 |
| WO | WO 2006/060634 A2 | 6/2006 |
| WO | WO 2007/005581 A2 | 1/2007 |

OTHER PUBLICATIONS

Chong et al, Biochem. Biophys. Res. Com'n (2000) 279:462-467.*
Peterson et al, Crop Sci. (1984) 24:390.*
Dweikat et al, Mol. Breeding (2005) 16:93-101.*
Kanampiu et al, Crop Protection (2001) 20:885-895.*
McCourt et al, PNAS (2006) 103:569-573.*
Miyata et al, J. Mol. Evol. (1979) 12:219-236.*
Chong et al., "Amino acid residues conferring herbicide tolerance in tobacco acetolactate synthase" Biochem. Biophys. Res. Comm. 279:462-467 (2000).
Dweikat, "A diploid, interspecific, fertile hybrid from cultivated sorghum, Sorghum bicolor, and the common Johnsongrass weed Sorghum halepense" Mol. Breeding 16:93-101 (2005).
Girijashankar et al., "Development of transgenic sorghum for insect resistance against the spotted stem borer (*Chilo partellus*)" Plant Cell Rep. 24:513-522 (2005).
Haughn et al., Transformation with a mutant *Arabidopsis* acetolactate synthase gene renders tobacco resistant to sulfonylurea herbicides Mol. Gen. Genet. 211:266-271 (1988).
Hennigh et al., "Postemergence weed control in acetolactate-resistant grain sorghum" Weed Technol. 24:219-225 (2010).
Hennigh et al., "Response of acetolactate synthase-resistant grain sorghum to nicosulfuron plus rimsulfuron" Weed Technol. 24:411-415 (2010).
Hennigh et al., "Weed control with selected herbicides in acetolactate synthase-resistant sorghum" Crop Protection 29:879-883 (2010).
King et al., "Herbicide programs for the control of ALS-resistant shattercane (*Sorghum bicolor*) in corn (*Zea mays*)" Weed Technol. 20:416-421 (2006).
K-State Extension Agronomy, "e-Updates", No. 75 (Mar. 30, 2007).
Mace et al., "Whole-genome sequencing reveals untapped genetic potential in Africa's indigenous cereal crop sorghum" Nature Comm. 4:2320 (2013).
Ochanda et al., "Selection before backcross during exotic germplasm introgression" Field Crops Res. 112:37-42 (2009).
Paterson et al., "The weediness of wild plants: molecular analysis of genes influencing dispersal and persistance . . . " PNAS USA 92:6127-6131 (1995).
Paterson et al., "The Sorghum bicolor genome and the diversification of grasses" Nature 457(29):551-556 (2009).
Peterson et al., "Registration of Tx2783 greenbug resistant sorghum germplasm line" Crop Sci. 24:390 (1984).
Rich et al., "Plant Genetic Resources—Striga resistance in the wild relatives of sorghum" 44:2221-2229 (2004).
Smith et al., "Functional expression of plant acetolactate synthase genes in *Escherichia coli*" PNAS USA 86:4179-4183 (1989).
Subramanian et al., "Acetolactate synthase inhibiting herbicides bind to the regulatory site" Plant Physiol. 96:310-313 (1991).
Tan et al., "Imidazolinone-tolerant crops: history, current status and future" Pest Management Sci. 61:246-257 (2005).
Zelaya et al., "Evolved resistance to acetolactate synthase-inhibiting herbicides. . . . in Iowa" Weed Sci. 52:538-548 (2004).
International Search Report in corresponding PCT/US2007/086612 dated Jul. 25, 2008.
European Communication issued in European Patent Application No. 07869010.4-2403, dated Sep. 9, 2012.

(Continued)

*Primary Examiner* — Mykola V. Kovalenko
(74) *Attorney, Agent, or Firm* — Potter Anderson and Corroon LLP

(57) ABSTRACT

The present invention provides for compositions and methods for producing *sorghum* crop plants that are resistant to herbicides. In particular, the present invention provides for *sorghum* plants, plant tissues and plant seeds that contain altered acetolactate synthase (ALS) genes and proteins that are resistant to inhibition by herbicides that normally inhibit the activity of the ALS protein.

7 Claims, 1 Drawing Sheet
Specification includes a Sequence Listing.

(56) References Cited

OTHER PUBLICATIONS

Non-final Office Action in U.S. Appl. No. 11/951,629, dated Jul. 16, 2010.
Final Office Action in U.S. Appl. No. 11/951,629, dated Mar. 30, 2011.
Advisory Action in U.S. Appl. No. 11/951,629, dated Jul. 8, 2011.
Non-final Office Action in U.S. Appl. No. 11/951,629, dated Jul. 12, 2013.
Final Office Action in U.S. Appl. No. 11/951,629, dated Jan. 13, 2014.
Advisory Action in U.S. Appl. No. 11/951,629, dated Mar. 19, 2014.
Non-final Office Action in U.S. Appl. No. 11/951,629, dated May 27, 2014.
Final Office Action in U.S. Appl. No. 11/951,629, dated Dec. 31, 2014.
Advisory Action in U.S. Appl. No. 11/951,629, dated Mar. 16, 2015.
Non-final Office Action in U.S. Appl. No. 11/951,629, dated Apr. 30, 2015.
Final Office Action in U.S. Appl. No. 11/951,629, dated Dec. 16, 2015.
Advisory Action in U.S. Appl. No. 11/951,629, dated Feb. 17, 2016.
Non-final Office Action in U.S. Appl. No. 11/951,629, dated Jun. 27, 2016.

* cited by examiner

| | | | | |
|---|---|---|---|---|
| | TA3960_4558 | 1631 | CCCAGTGAAGTCTTTGTGCTAAACAACCAGCACCTGGGATGGTGTGCAGTGGAGGACAGGTTCTATAAGGCCAATAGAG | SEQ ID NO: 5 |
| Tx623 | (c)_22_F4r_Tx623 | 500 | CCCAGTGAAGTCTTTGTGCTAAACAACCAGCACCTGGGATGGTGTGCAGTGGAGGACAGGTTCTATAAGGCCAATAGAG | SEQ ID NO: 6 |
| Tx623 | 32_B5_Tx623 | 473 | CCCAGTGAAGTCTTTGTGCTAAACAACCAGCACCTGGGATGGTGTGCAGTGGAGGACAGGTTCTATAAGGCCAATAGAG | SEQ ID NO: 7 |
| Tx430 | 9_B5_Tx430 | 471 | CCCAGTGAAGTCTTTGTGCTAAACAACCAGCACCTGGGATGGTGTGCAGTGGAGGACAGGTTCTATAAGGCCAATAGAG | SEQ ID NO: 8 |
| S1-1 | 10_B5_S1-1 | 477 | CCCAGTGAAGATCTTTGTGCTAAACAACCAGCACCTGGGATGGTGTGCAGTGGAGGACAGGTTCTATAAGGCCAATAGAG | SEQ ID NO: 9 |
| S1-2 | 11_B5_S1-2 | 472 | CCCAGTGAAGATCTTTGTGCTAAACAACCAGCACCTGGGATGGTGTGCAGTGGAGGACAGGTTCTATAAGGCCAATAGAG | SEQ ID NO: 10 |
| S1-3 | 12_B5_S1-3 | 474 | CCCAGTGAAGATCTTTGTGCTAAACAACCAGCACCTGGGATGGTGTGCAGTGGAGGACAGGTTCTATAAGGCCAATAGAG | SEQ ID NO: 11 |
| S1-3 | (c)_21_F4r_S1-3 | 502 | CCCAGTGAAGATCTTTGTGCTAAACAACCAGCACCTGGGATGGTGTGCAGTGGAGGACAGGTTCTATAAGGCCAATAGAG | SEQ ID NO: 12 |

ACETOLACTATE SYNTHASE HERBICIDE RESISTANT SORGHUM

The present application claims priority to U.S. Provisional Patent Application No. 60/873,529 filed Dec. 7, 2006, incorporated herein by reference in its entirety.

FIELD OF THE INVENTION

The present invention provides for compositions and methods for producing *sorghum* cultivars that are resistant to herbicides. In particular, the present invention provides for *sorghum* plants, plant tissues and plant seeds that contain altered acetolactate synthase (ALS) genes and proteins that are resistant to inhibition by herbicides that normally inhibit the activity of the ALS protein.

BACKGROUND OF THE INVENTION

*Sorghum* is the second most important cereal-feed grain grown in the United States. Production is economically critical to farms operating in marginal rainfall areas because of *sorghum*'s ability to tolerate drought and heat. Both the livestock and bio-energy industries utilize *sorghum* as an energy substrate thereby making it a versatile crop.

Worldwide, *sorghum* is the fifth leading cereal grain. As it is tolerant to both drought and heat, it is easily the most widely grown food grain in the semiarid regions of sub-Sahelian Africa and in the dry central peninsular region of India. As such, *sorghum* is used in human consumption in most of the driest regions of the world thereby making it a critically important food crop in these locations.

The development of herbicide resistance in plants offers significant production and economic advantages, as such the use of herbicides for controlling weeds in crops has become almost a universal practice. However, application of such herbicides can also result in death or reduced growth of the desired crop plant, making the time and method of herbicide application critical or in some cases unfeasible.

Of particular interest to farmers is the use of herbicides with greater potency, broad weed spectrum effectiveness and rapid soil degradation. Plants, plant tissues and seeds with resistance to these compounds provide an attractive solution by allowing the herbicides to be used to control weed growth, with small risk of damage to the crop. One such class of broad-spectrum herbicides are those that inhibit the activity of the acetolactate synthase (ALS) enzyme in a plant. Acetolactate synthase is required for the production of essential amino acids such as valine, leucine and isoleucine in plants (this biochemical pathway is not present in humans or other animals). *Sorghum* is susceptible to many ALS inhibiting herbicides that target monocot species, making the use of these herbicides to control grassy weeds almost impossible, as they will also inhibit the growth of the crop plant.

Acetolactate synthase herbicides control a wide spectrum of grass and broadleaf weeds at very low application rates. There are currently over 56 different ALS herbicides available, made from various formulations of sulfonylureas (SU), imidazolinones (IMI), triazolopyrimidines (TP) and pyrimidinylthiobenzoates (PTB). Mutations in some crop plants, for example tobacco, corn (U.S. Pat. No. 5,767,361) and soybeans, have been found that confer ALS herbicide resistance, however, to date no such discovery has been found in *sorghum* (for a review, see Tan et al., 2005, Pest. Manag. Sci. 61:246-257). Due to the importance of *sorghum* on the world stage, what are needed are *sorghum* cultivars that are resistant to the inhibitory effects of ALS herbicides, thereby allowing for greater crop yield when these herbicides are used to control grassy weeds.

SUMMARY OF THE INVENTION

The present invention provides for compositions and methods for producing *sorghum* cultivars that are resistant to herbicides. In particular, the present invention provides for *sorghum* plants, plant tissues and plant seeds that contain altered acetolactate synthase (ALS) genes and proteins that are resistant to inhibition by herbicides that normally inhibit the activity of the ALS protein.

Cultivated *sorghum* [*Sorghum bicolor* (L.) Moench] is susceptible to many ALS inhibiting herbicides that target monocot, or grassy, species. However, as described herein a *sorghum* genotype was found that exhibits resistance to ALS herbicides. Genetic analysis has identified genetic differences in the *sorghum* germplasm that result in an ALS herbicide resistance phenotype.

In one embodiment, the invention provides for one or more *sorghum* plants whose germplasm comprises a mutation that renders the plant resistant to ALS herbicides. Moreover, in further embodiments, the invention relates to the offspring (e.g., F1, F2, F3, etc.) of a cross of said plant wherein the germplasm of said offspring has the same mutation as the parent plant. Therefore, embodiments of the present invention provide for *sorghum* hybrids whose germplasm contains a mutation, such that the phenotype of the plants is ALS herbicide resistance.

In one embodiment, the present invention provides a *sorghum* hybrid wherein said *sorghum* hybrid germplasm confers resistance to inhibition by one or more acetolactate synthase herbicides at levels of said one or more herbicides that would normally inhibit the growth of a *sorghum* hybrid. In some embodiments, said one or more acetolactate synthase herbicides are from a group consisting of sulfonylureas, imidazolinones, trazolopyrimides and pyrimidinylthiobenzoates. In some embodiments, said *sorghum* hybrid germplasm that confers resistance to inhibition by one or more acetolactate synthase herbicides comprises mutations in the acetolactate gene as found in ATCC No. PTA-7999. In some embodiments, seeds from said *sorghum* hybrid are coated with an acetolactate synthase herbicide.

In one embodiment, the present invention provides a method of controlling weeds in the vicinity of a *sorghum* hybrid as described herein, comprising providing one or more acetolactate synthase herbicides, applying said one or more acetolactate synthase herbicides to a field comprising a *sorghum* hybrid as described herein, and controlling weeds in the vicinity of said *sorghum* hybrid such that weed growth is adversely affected by the application of said one or more herbicides and growth of said *sorghum* hybrid is not adversely affected. In some embodiments, said one or more acetolactate synthase herbicides are from a group consisting of sulfonylureas, imidazolinones, trazolopyrimides and pyrimidinylthiobenzoates. In some embodiments, said *sorghum* hybrid comprises one or more mutations in the acetolactate synthase gene as found in ATCC No. PTA-7999.

In one embodiment, the present invention provides a *sorghum* hybrid, wherein said *sorghum* hybrid comprises a germplasm comprising one or more mutations in the acetolactate synthase gene such that resistance to one or more acetolactate synthase herbicides is conferred to said hybrid. In some embodiments, said *sorghum* hybrid is created by introgression of a *sorghum* germplasm that comprises said one or more mutations for conferring resistance to one or more acetolactate synthase herbicides. In some embodiments, said *sorghum* hybrid is created by incorporation of a heterologous gene comprising one or more mutations for conferring resistance to one or more acetolactate synthase herbicides.

In one embodiment, the present invention provides a method for producing a *sorghum* hybrid plant line resistant to one or more acetolactate synthase herbicides comprising identifying a germplasm conferring said herbicide resistance, wherein said herbicide resistant germplasm derives from an herbicide resistant *sorghum* plant, and introducing said germplasm into an elite *sorghum* plant line. In some embodiments, said introducing of said germplasm into said elite *sorghum* plant line is by introgression. In some embodiments, said introducing of said germplasm into said elite *sorghum* plant line is by introduction of a heterologous gene.

In one embodiment, the present invention provides a *sorghum* hybrid wherein the germplasm of said hybrid comprises conferred resistance to one or more acetolactate synthase herbicides and resistance to one or more compounds from one or more herbicide groups that are not acetolactate synthase inhibitors.

In one embodiment, the present invention provides a method for identifying *sorghum* plant lines resistant to acetolactate synthase herbicides comprising supplying a nucleic acid sample for a *sorghum* plant, providing amplification primers for amplifying a region of a *sorghum* plant corresponding to an acetolactate synthase gene present in said nucleic acid sample, applying said amplification primers to said nucleic acid sample such that amplification of said region of said acetolactate synthase gene occurs, and identifying *sorghum* plants resistant to acetolactate synthase herbicides based on the presence of one or more mutations that confer acetolactate synthase herbicide resistance present in said amplified nucleic acid sample.

In one embodiment, the present invention provides for *sorghum* seeds wherein said germplasm of said seeds comprises a mutant acetolactate synthase gene such that said mutation confers resistance to inhibition by acetolactate synthase herbicidices. In some embodiments, the germplasm of said *sorghum* seeds comprise a mutant acetolactate synthase gene as found in ATCC No. PTA-7999. In some embodiments, the mutant acetolactate synthase gene is a functional fragment of the gene as found in ATCC No. PTA-7999, such that the gene fragment encodes a protein fragment that is sufficient to confer resistance to inhibition by acetolactate synthase herbicides to a *sorghum* plant. In some embodiments, the present invention provides for *sorghum* plants that grow from said seeds and further plant parts that comprise said *sorghum* plants grown from said seeds.

In one embodiment, the present invention further provides for *sorghum* hybrid plants that have all the physiological and morphological characteristics of said *sorghum* plant grown from said *sorghum* seed. In further embodiments, the present invention provides for tissue cultures and regenerated tissue cultures that arise from said *sorghum* seed or said *sorghum* plant part that comprises a mutation in said acetolactate synthase gene as found in ATCC No. PTA-7999.

In some embodiments, the present invention provides for a *sorghum* hybrid that comprises a gene that is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419 as found in ATCC No. PTA-7999. In some embodiments, the ALS herbicide resistant gene that is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419 comprises one or more of the amino acid substitutions $Val_{531}Ile$ and $Trp_{545}Leu$, for example, as found in SEQ ID NO: 1.

In one embodiment, the present invention provides a method of producing *sorghum* seed comprising crossing a plant comprising a mutant acetolactate synthase gene as found in ATCC No. PTA-7999 with itself or a second *sorghum* plant and collecting said seed from said cross. In some embodiments, the methods for producing said *sorghum* seed comprises planting a parent seed *sorghum* line wherein said parent seed line comprises a germplasm that confers resistance to acetolactate synthase herbicides with a parent pollinator *sorghum* line wherein said pollinator seed line germplasm comprises a germplasm that confers resistance to acetolactate synthase herbicides, growing said parent seed and pollinator *sorghum* plants together, allowing for the said parent seed plants to be pollinated by said parent pollinator plants, and harvesting the seed that results from said pollination.

DESCRIPTION OF THE FIGURES

FIG. 1 is a sequence alignment that shows the double mutation of $Val_{531}Ile$ and $Trp_{545}Leu$ in the *sorghum* ALS gene found to be associated with ALS herbicide resistance. Genomic DNA from *sorghum* plants was PCR amplified in the region containing the nucleotides encoding for $Val_{531}$ and $Trp_{545}$ and then sequenced. The sequence alignment in this region is shown using the wild type *S. bicolor* sequence (SEQ ID NO: 5) as a reference. Also shown is the sequence for ALS herbicide sensitive *sorghum* varieties Tx623 (SEQ ID: 6 and SEQ ID NO:7) and Tx430 (SEQ ID NO: 8) as compared to ALS herbicide resistant *sorghum* varieties 51-1 (SEQ ID NO: 9), S1-2 (SEQ ID NO: 10), and S1-3 (SEQ ID NO:11 and SEQ ID NO: 12). The boxes indicate the codons encoding the $Val_{531}$ and $Trp_{545}$ residues or the $Val_{531}Ile$ and Trps4sLeu amino acid substitutions.

DEFINITIONS

As used herein, the term "resistant" and "tolerant" is used to refer to plants, for example *sorghum* plants, that are able to tolerate conditions (e.g., herbicides such as ALS herbicides) harmful to other strains of the same species.

As used herein, the term "cultivar" is synonymous with "variety" and is used to refer to crop plants that are a group of similar plants that by structural features and performance can be identified from other cultivars within the same species.

As used herein, the term "hybrid" refers to the offspring or progeny of genetically dissimilar plant parents or stock produced as the result of controlled cross-pollination as opposed to a non-hybrid seed produced as the result of natural pollination.

As used herein, the term "progeny" refers to generations of a plant, wherein the ancestry of the generation can be traced back to said plant.

As used herein, the term "derivative" of an herbicide resistant plant includes both the progeny of that herbicide resistant plant, as well as any mutant, recombinant, or genetically engineered derivative of that plant, whether of the same species or a different species, where the herbicide resistant characteristic(s) of the original herbicide resistant plant has been transferred to the derivative plant.

As used herein, the term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, and a cell. In some embodiments of the present invention transgenic plants are crop plants.

As used herein, the terms "F-generation" and "filial generation" refers to any of the consecutive generations of plants, cells, tissues or organisms after a biparental cross. The generation resulting from a mating of a biparental cross (i.e. two parents) is the first filial generation (designated as "F1" and "$F_1$") in reference to a seed and its plant, while that resulting from crossing of F1 individuals is the second filial generation (designated as "F2" or "$F_2$") in reference to a seed and its plant.

As used herein, the term "germplasm" refers to any genetic material of plants that contains functional units of heredity. The twit "elite germplasm" in reference to a plant refers to hereditary material of proven genetic superiority.

As used herein, the term "elite plant," refers to any plant that has resulted from breeding and selection for superior agronomic performance. For example, elite *sorghum* plants referred to herein include, but are not limited to, Tx430, Tx2737, Tx2783, 00MN7645, HP162, Wheatland, Tx3042, OK11, QL41 and Tx643, Bt *sorghum* lines.

As used herein, the term "trait" or "phenotype" refers to an observable and/or measurable characteristic of an organism. For example, the present invention describes plants that are ALS herbicide resistant.

As used herein, the term "ALS herbicide", also known as AHAS herbicide, refers to a herbicide that inhibits the activity of the acetolactate synthase (also known as acetohydroxyacid synthase) enzyme in a plant. Examples of ALS herbicides as described herein include, but are not limited to, sulfonylureas (SU), imidazolinones (INI), triazolopyrimidines (TI) and pyrimidinylthiobenzoates.

As used herein, the terms "marker" and "DNA marker" and "molecular marker" in reference to a "selectable marker" refers to a physiological or morphological trait that may be determined as a marker for its own selection or for selection of other traits closely linked to that marker. For example, such a marker could be a gene or trait that associates with herbicide tolerance including, but not limited to, simple sequence repeat (SSR), single nucleotide polymorphism (SNP), genetic insertions and/or deletions and the like.

As used herein, the term "introgress" and "introgressing" and "introgression" refers to conventional (i.e. classic) pollination breeding techniques to incorporate foreign genetic material into a line of breeding stock. For example, the present invention provides for *sorghum* crop plants introgressed with a mutant ALS gene for herbicide tolerance by crossing two plant generations.

As used herein, the term "wild-type" when made in reference to a gene refers to a functional gene common throughout a plant population. A functional wild-type gene is that which is most frequently observed in a population and is thus arbitrarily designated the "normal" or "wild-type" form of the gene.

As used herein, the terms "modified" or "mutant" or "functional mutant" when made in reference to a gene or to a gene product refers, respectively, to a gene or to a gene product which displays modifications in sequence and/or functional properties (i.e., altered characteristics) when compared to the wild-type gene or gene product. Thus, the terms "modified" and "mutant" when used in reference to a nucleotide sequence refer to an nucleic acid sequence that differs by one or more nucleotides from another, usually related nucleotide acid sequence and the term "functional mutant" when used in reference to a polypeptide encodes by said "modified" or "mutant" nucleic acid refers to the protein or polypeptide that retains activity. In the present application, the ALS mutant protein, "or functional mutant" thereof is an ALS gene that retains its native activity to create essential amino acids. Additionally, a "modified" nucleotide sequence is interpreted as that found in the degenerate genetic code as known by those skilled in the art. For example, the genetic code is degenerate as there are many instances in which different codons specify the same amino acid; a genetic code in which some amino acids may each be encoded by more than one codon. It is contemplated that the present invention comprises such degeneracy (e.g., wherein a *sorghum* hybrid comprises an ALS gene that is at least 70% homologous, at least 80% homologous, at least 85% homologous, at least 90% homologous, at least 95% homologous, at least 97% homologous, or at least 99% homologous to SEQ ID NO: 1) as found in, for example, the *sorghum* germplasm.

As used herein, the term "heterologous" when used in reference to a gene or nucleic acid refers to a gene that has been manipulated in some way.

As used herein, the term "portion" or "functional fragment" when used in reference to a protein (as in "a fragment of a given protein" or "a protein fragment") refers to fragments of that protein. The fragments may range in size from four amino acid residues to the entire amino sequence minus one amino acid. In the present invention, the protein fragment is preferentially functional such that the protein fragment confers resistance to inhibition to acetolactate synthase herbicides to a given plant.

DETAILED DESCRIPTION OF THE INVENTION

In one embodiment, the present invention provides genes encoding altered ALS genes and proteins. In some embodiments, the present invention provides for the use of herbicides that do not inhibit the ALS enzyme in *sorghum* that contains an altered ALS enzyme in order to reduce the amount of monocot and dicot weed plants present in a crop field, wherein said weed plants are susceptible to ALS herbicides.

In one embodiment, the present invention provides an ALS resistant germplasm of a *sorghum* plant resulting from, for example, a cross between two parent plants, a wild *sorghum* "Tailwind or Tw" and the elite pollinator plant line Tx2783, yielding an $F_1$ generation, followed by two backcrosses ($BC_2F_3:F_4$), with the resultant seed being deposited under ATCC No: PTA-7999, designated KSU 06MN8419.

In one embodiment, the present invention provides a *sorghum* germplasm that confers resistance to inhibition by ALS herbicides and also confers insect resistance against the spotted stem borer *Chilo partellus* (Girijashankar et al., 2005, Plant Cell Rep. 24:513-522, incorporated herein in its entirety). For example, a *sorghum* hybrid whose germplasm comprises a synthetic cryl Ac gene from *Bacillus thuringi-*

*ensis* (Bt) is introgressed into a *sorghum* line whose germplasm confers resistance to ALS herbicides. As well, the incorporation of ALS herbicide resistance and insect resistance is accomplished via plant transgenesis into the same *sorghum* hybrid. One skilled in the art will recognize the various techniques as described herein that are applicable to the incorporation of two or more resistance attributes into the same *sorghum* hybrid.

In one embodiment, the ALS herbicide resistant gene as found in *sorghum* comprising ALS germplasm KSU 06MN8419 deposited under ATCC No: PTA-7999 is incorporated into elite *sorghum* varieties through plant breeding and selection, thereby providing for the development of herbicide resistant crop varieties that will tolerate the use of ALS inhibiting herbicides for weed control. In some embodiments, the ALS resistant herbicide gene is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419. In some embodiments, the ALS herbicide resistant gene that is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419 comprises one or more of the amino acid substitutions $Val_{531}$Ile and $Trp_{545}$Leu. Deployment of this herbicide resistance trait in the aforementioned crop plant varieties allows use of these herbicides to control monocot and dicot weeds that grow in the presence of these crops. In some embodiments, the incorporation of the ALS resistance germplasm into elite lines is via introgression, or classical breeding methods. In some embodiments, the incorporation of the ALS resistance gene into elite lines is via heterologous gene transgenesis. In some embodiments, the invention provides a *sorghum* hybrid, wherein at least one ancestor of said *sorghum* hybrid is derived from the ALS resistant germplasm designated KSU 06MN8419 deposited under ATCC No: PTA-7999. In some embodiments, the present invention provides a *sorghum* hybrid, wherein at least one ancestor of said *sorghum* hybrid comprises the acetolactate synthase gene that confers resistance to ALS herbicides as found in the germplasm designated KSU 06MN8419 deposited under ATCC No: PTA-7999. In some embodiments, the ALS resistant herbicide gene as found in a *sorghum* hybrid is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419. In some embodiments, the ALS herbicide resistant gene that is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419 comprises one or more of the amino acid substitutions $Val_{531}$Ile and $Trp_{545}$Leu.

In some embodiments, ALS herbicide resistance germplasm is introgressed into an elite *sorghum* line using classic breeding techniques. Examples of classical breeding methods for *sorghum* can be found in, for example, Sleper and Poehlman, 2006, Breeding Field Crops, Fifth Edition, Blackwell Publishing, incorporated by reference herein in its entirety.

In one embodiment, the ALS herbicide resistance germplasm is introgressed into a *sorghum* plant that provides food for human consumption. In some embodiments, the ALS herbicide resistance germplasm is introgressed into *sorghum* plants that provide food for livestock (e.g., poultry, cattle, swine, sheep, etc). In one embodiment, the ALS herbicide resistance gene is introduced into the plant genome via transgenesis using vectors and technologies known in the art.

In one embodiment, the present invention provides methods for controlling weeds in a field of *sorghum* crop plants. In some embodiments, controlling the weeds comprises applying an ALS herbicide to said field of *sorghum* crop plants, such that weed growth is inhibited but *sorghum* plant growth is not adversely affected. In some embodiments, the ALS herbicide being applied is from the sulfonylurea herbicide family, comprising one or more of the active ingredients amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazolsulfuron, iodosulfuron-methyl-sodium, mesosulfuron-methyl, metsulfuron-methyl, nicosulfuron, oxasulfuron, primisulfuron-methyl, pyraxosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, triofensulfuron, and tritosulfuron. In some embodiments, the ALS herbicide being applied is from the imidazolinone herbicide family, comprising one or more of the active ingredients imazamethabenz-methyl, imazamox, imazapic, imizapyr, imizaquin, and imazethapyr. In some embodiments, the ALS herbicide being applied is from the pyrimidinylthiobenzoate herbicide family, comprising one or more of the active ingredients bispyribac-sodium, pyribenzoxim, pyriftalid, pyriminobac-methyl, and pyrithiobac-sodium. In some embodiments, the ALS herbicide being applied is from the triazolopyrimidine herbicide family, comprising one or more of the active ingredients cloransulam-methyl, diclusolam, florasulam, flumetsulam, metosulam, and penoxsulam. In some embodiments, the ALS herbicide being applied comprises a combination of active ingredients from one or more ALS herbicide families as disclosed herein. However, the present application is not limited to the ALS herbicide used, and a skilled artisan will appreciate that new chemicals are being discovered at any given time that inhibit the ALS enzyme.

In one embodiment, the present invention provides use of a transgene comprising a heterologous gene such as a gene encoding a mutant ALS protein for providing the selected agronomic trait of ALS herbicide resistance. In one embodiment, the transgene comprises a mutant ALS gene as found in the germplasm KSU 06MN8419 deposited under ATCC No: PTA-7999. In some embodiments, the ALS gene is at least 70% homologous, at least 80% homologous, at least 85% homologous, at least 90% homologous, at least 95% homolous, at least 97% homologous, or at least 99% homologous to the mutant ALS gene as found in the germplasm KSU 06MN8419. In some embodiments, the mutant ALS gene that is at least 70% homologous, at least 80% homologous, at least 85% homologous, at least 90% homologous, at least 95% homologous, at least 97% homologous, or at least 99% homologous to the mutant ALS gene as found in the germplasm KSU 06MN8419 comprises one or more of the amino acid substitutions $Val_{531}$Ile and $Trp_{545}$Leu.

*Striga* commonly known as witchweed, is a genus of noxious parasitic plants of grasses and monocot cereal crops, such as maize, wheat and *sorghum*. A heavy infestation of *Stiga* in a field of crop plants damages the host plants, causing stunting, chlorosis, wilting, and ultimately host plant death, especially in its native habitat where water can be scarce. *Striga* is native to semiarid and temperate grassland regions of Africa and Asia, however it can flourish outside its natural range, and current infestations exist on agricultural lands in the United States. Infestations are widespread in Africa, therefore *Stiga* is an ongoing problem for farmers in semi-arid and sub-sahelian regions where *sorghum* is a main food crop. The parasitic plant is difficult to eradicate, as its seeds can lie dormant in the soil for up to ten years prior to germination.

Biological signals for *Striga* seed germination include being stimulated by root exudates from their host plant. *Striga* seeds germinate by sending an infective structure to the host that attaches to the host root and invades the host vascular system, thereby robbing the host of water, minerals and carbohydrates. Once initial contact with the host is made, initiation of *Striga* shoot and additional roots begins, and the theft from the host plant increases. In native locations where water is scarce, *Striga* effectively drains the host plant of minerals and water.

*Striga* parasitism is inhibited by ALS herbicides. The present invention is not limited to a particular mechanism. Indeed, an understanding of the mechanism is not necessary to practice the present invention. Nonetheless, *Striga* infection of *sorghum* roots is eliminated by coating *sorghum* seeds with ALS herbicides prior to planting. In one embodiment, the seeds of a *sorghum* hybrid comprising a germplasm that confers ALS herbicide resistance to said *sorghum* hybrid are coated with one or more ALS herbicides prior to planting. In some embodiments, the coated seeds are planted on agricultural land wherein resides *Striga* parasitic plant species. In some embodiments, the *sorghum* hybrid plants that grow from said coated seed are resistant to infection by *Striga*.

In one embodiment, the present invention provides for a *sorghum* hybrid whose germplasm confers resistance to ALS herbicides and resistance to one or more additional herbicides from one or more different herbicide groups. For example, additional herbicide groups used to inhibit weed growth, include, but are not limited to, inhibitors of lipid synthesis (e.g., aryloxyphenoxypropionates, cyclohexanodeiones, benzofuranes, chloro-carbonic acids, phosphorodithioates, thiocarbamates), inhibitors of photosynthesis at photosystem H (e.g., phenyl-carbamates, pyridazinones, triazines, triazinones, triazolinones, uracils, amides, ureas, benzothiadiazinones, nitriles, phenyl-pyridines), inhibitors of photosynthesis at photosystem I (e.g., bipyridyliums), inhibitors of protoporphyrinogen oxidase (e.g., diphenylethers, N-phenylphthalimides, oxadiazoles, oxyzolidinediones, phenylpyrazoles, pyrimidindiones, thiadiazoles), inhibitors of carotenoid biosynthesis (e.g., pyridazinones, pyridinecarboxamides, isoxazolidinones, triazoles), inhibitors of 4-hydroxyphenyl-pyruvate-dioxygenase (e.g., callistemones, isoxazoles, pyrazoles, triketones), inhibitors of EPSP synthase (e.g., glycines), inhibitors of glutamine synthetase (e.g., phosphinic acids), inhibitors of dihydropteroate synthase (e.g., carbamates), inhibitors of microtubule assembly (e.g., benzamides, benzoic acids, dinitroanilines, phosphoroamidates, pyridines), inhibitors of cell division (e.g., acetamides, chloroacetamides, oxyacetamides), inhibitors of cell wall synthesis (e.g., nitriles, triazolocarboxamides) and inhibitors of auxin transport (e.g., phthalamates, semicarbazones).

Classical Breeding of *Sorghum*

Field crops have been classically bred through techniques that take advantage of the plants method(s) of pollination. A plant is considered "self-pollinating" if pollen from one flower can be transmitted to the same or another flower, whereas plants are considered "cross-pollinated" if the pollen has to come from a flower on a different plant in order for pollination to occur.

Plants that are self-pollinated and selected over many generations become homozygous at most, if not all, of their gene loci, thereby producing a uniform population of true breeding progeny. A cross between two homozygous plants from differing backgrounds or two different homozygous lines will produce a uniform population of hybrid plants that will more than likely be heterozygous at a number of the gene loci. A cross of two plants that are each heterozygous at a number of gene loci will produce a generation of hybrid plants that are genetically different and are not uniform.

*Sorghum* plants are self-pollinating plants, but they can also be bred by cross-pollination. The development of *sorghum* hybrids requires the development of pollinator parents (fertility restorers) and seed parent inbreds using the cytoplasmic male sterility-fertility restorer system, the crossing of seed parents and pollinator parents, and the evaluation of the crosses. Pedigree breeding programs combine desirable traits; in the present application the desirable trait being plant resistance to ALS herbicides. This trait is introduced into the breeding pool from one or more lines, such that new inbred lines are created by crossing, followed by selection of plants with the desired trait, followed by more crossing, etc. New inbreds are crossed with other inbred lines (e.g., elite plant lines like those described herein).

Pedigree breeding starts with the crossing of two genotypes, such as Tailwind and an elite *sorghum* line (e.g., Tx430, Tx2737, Tx2783, 00MN7645, HP162, Wheatland, Tx3042, OK11, QL41, Tx643 and Bt *sorghum*). If the original two parents do not provide all of the desired characteristics, then other sources can be included in the breeding population. For example, if a hybrid is desired such that both ALS herbicide resistance and resistance to another herbicide as described herein is desirous, then plants with both these attributes could be crossed using classical breeding techniques. In the pedigree method, superior plants are selfed and selected in successive generations. In the succeeding generations, the heterozygous condition gives way to homogeneous lines as a result of self-pollination and selection. Typically, in the pedigree method, five or more generations of selfing and selection are practiced (e.g., S1, S2, S3, S4, S5, etc.).

Backcrossing is used to improve a plant line. Backcrossing transfers a specific desirable trait from one source to another that lacks the trait. This is accomplished by, for example, crossing a donor (for example, Tailwind) to an inbred line (e.g., Tx2783, an elite pollinator line as described herein). The progeny of this cross is then crossed back (i.e. backcrossing) to the elite inbred line, followed by selection in the resultant progeny for the desired trait (e.g., resistance to ALS herbicides). Following five or more backcross generations with selection for the desired trait the progeny are typically heterozygous for the locus (loci) controlling the desired phenotype, but will be like the elite parent for the other genetic traits. The last backcrossing is typically selfed in order to give a pure breeding progeny for the gene being transferred.

In current hybrid introgressive *sorghum* breeding programs, new parent lines are developed to be either seed-parent lines (e.g., Wheatland, Tx3042, N223, 01MN1589, 03MN954, OK11, QL41 and Tx643) or pollen-parent lines (e.g., Tx430, Tx2737, Tx2783, R45, 00MN7645 and HP162) depending on whether or not they contain fertility-restoring genes; the seed-parent lines do not have fertility restoring genes and are male-sterile in certain cytoplasms (also known as "A-line" plants) and male fertile in other cytoplasms (also known as "B-line" plants), whereas the pollen-parent lines are not male sterile and do contain fertility restoring genes (also known as "R-line" plants). The seed-parent lines are typically created to be cytoplasmically male sterile such that the anthers are minimal to non-existant in these plants thereby requiring cross-pollination. The seed-parent lines will only produce seed, and the cytoplasm is transmitted only through the egg. The pollen for cross pollination is furnished through the pollen-parent lines that contain the genes necessary for complete fertility restoration in the F1 hybrid, and the cross combines with the male sterile seed parent to produce a high-yielding single cross hybrid with good grain quality. Examples of R-line and B-line plants that find utility in the present invention include, but are not limited to, those described in Table 1.

TABLE 1

| Pedigree | New Source | Gen | Comments |
| --- | --- | --- | --- |
| Tx2737///Tx2737//90SN7/Tw | MN07-1903 | BC2F5 | R-line |
| Tx2737///Tx2737//90SN7/Tw | MN07-1905 | BC2F5 | R-line |
| Tx430///Tx2737//90SN7/Tw | MN07-1916 | BC2F5 | R-line |
| Tx430///Tx2737//90SN7/Tw | MN07-1926 | BC2F5 | R-line |
| Tx430///Tx2737//90SN7/Tw | MN07-1935 | BC2F4 | R-line |
| Tx430///Tx2737//90SN7/Tw | MN07-1936 | BC2F4 | R-line |
| Tx430///Tx2737//90SN7/Tw | MN07-1940 | BC2F4 | R-line |
| Tx430///Tx2737//90SN7/Tw | MN07-1941 | BC2F4 | R-line |
| Tx430///Tx2737//90SN7/Tw | MN07-1944 | BC2F4 | R-line |
| Tx430///Tx2737//90SN7/Tw | MN07-1945 | BC2F4 | R-line |
| Tx430///Tx2737//90SN7/Tw | MN07-1956 | BC2F4 | R-line |
| Tx2737///Tx2737//90SN7/Tw | MN07-1981 | BC2F3 | R-line |
| Tx2737///Tx2737//90SN7/Tw | MN07-1984 | BC2F3 | R-line |
| Tx430///Tx2737//90SN7/Tw | MN07-1987 | BC2F3 | R-line |
| Tx430///Tx2737//90SN7/Tw | MN07-1992 | BC2F3 | R-line |
| Tx430///Tx2737//90SN7/Tw | MN07-1995 | BC2F3 | R-line |
| R45////R45///Tx2737//90SN7/Tw | MN07-2013 | BC2F3 | R-line |
| Tx2783//Tx2783/Tw | MN07-2075 | BC2F4 | R-line |
| N223///N223//N223/Tw | MN07-2094 | BC2F6 | B-line |
| Wheatland///N223//N223/Tw | MN07-2113 | BC2F4 | B-line |
| Wheatland///N223//N223/Tw | MN07-2118 | BC2F4 | B-line |
| N223///N223//N223/Tw | MN07-2134 | BC2F5 | B-line |
| N223///N223//N223/Tw | MN07-2136 | BC2F5 | B-line |
| OK11/////OK11///N223//N223/Tw | MN07-2164 | BC3F3 | B-line |
| QL41/////QL41/////OK11///N223//N223/Tw | MN07-2198 | BC4F3 | B-line 75% DPI (QL41) |
| 01MN1589/////Wht///N223//N223/Tw | MN07-2230 | BC4F3 | B-line |
| 01MN1589/////Wht///N223//N223/Tw | MN07-2248 | BC3F3 | B-line |
| 01MN1589/////Wht///N223//N223/Tw | MN07-2251 | BC3F3 | B-line |
| 01MN1589/////Wht///N223//N223/Tw | MN07-2254 | BC3F3 | B-line |
| 03MN954/////Wht///N223//N223/Tw | MN07-2261 | BC3F3 | B-line |
| Tx3042//////Tx3042/////N223///N223//N223/Tw | MN07-2290 | BC4F3 | B-line |
| Tx3042//////Tx3042/////N223///N223//N223/Tw | MN07-2293 | BC4F2 | B-line |
| N223///N223//N223/Tw | MN07-2084 | BC2F4 | B-line |
| N223///N223//N223/Tw | MN07-2088 | BC2F4 | B-line |

Typically, this cytoplasmic male sterility-fertility restorer system is performed for the production of hybrid seed by planting blocks of rows of male sterile (seed-parent) plants and blocks of rows of fertility restorer (pollen-parent) plants, such that the seed-parent plants are wind pollinated with pollen from the pollen-parent plant. This process produces a vigorous single-cross hybrid that is harvested and planted by the consumer. Male sterile, seed-parent plants can also be created by genetically breeding recessive male-sterile nuclear genes into a particular population, however the cytoplasmic male sterility-fertility restorer system is typically the system used for breeding hybrid *sorghum*. Sleper and Poehlman, 2006, Breeding Field Crops, Fifth Ed., Blackwell Publishing provides a good review of current *sorghum* breeding procedures and is incorporated herein in its entirety.

The present invention is not limited to the elite parent *sorghum* lines listed, and one skilled in the art will recognize that any elite *sorghum* line would be equally amenable to the compositions and methods as described herein.

Plant Transgenics

Heterologous genes intended for expression in plants are first assembled in expression vectors containing a heterologous gene and appropriate transcriptional and translational control elements, methods of which are well known to those skilled in the art. Methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., herein incorporated by reference).

In general, these vectors comprise a nucleic acid sequence encoding a heterologous gene operably linked to a promoter and other regulatory sequences (e.g., enhancers, polyadenylation signals, etc.) required for expression in a plant.

Promoters include, but are not limited to, constitutive promoters, tissue-, organ-, and developmentally-specific promoters, and inducible promoters. Examples of promoters include, but are not limited to; constitutive promoter 35S of cauliflower mosaic virus; a wound-inducible promoter from tomato, leucine amino peptidase (Chao et al., 1999, Plant Physiol 120:979-992, herein incorporated by reference in its entirety); a chemically-inducible promoter from tobacco, Pathogenesis-Related 1 (induced by salicylic acid and benzothiadiazole-7-carbothioic acid S-methyl ester); a heat shock promoter (U.S. Pat. No. 5,187,267, herein incorporated by reference in its entirety); a tetracycline-inducible promoter (U.S. Pat. No. 5,057,422, herein incorporated by reference in its entirety); and seed-specific promoters.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters such as those disclosed herein. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (Odell et al., 1985, Nature 313:810; Rosenberg et al., 1987, Gene, 56:125; Guerineau et al., 1991, Mol. Gen. Genet. 262:141; Proudfoot, 1991, Cell, 64:671; Sanfacon et al., 1990, Genes Dev. 5:141; Mogen et al., 1990, Plant Cell, 2:1261; Munroe et al., 1990, Gene, 91:151; Ballas et al., 1989, Nucleic Acids Res. 17:7891; Joshi et al., 1987, Nucleic Acid Res., 15:9627, all of which are incorporated herein by reference in their entireties).

In some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. Intron sequences have been routinely incorporated into plant transformation vectors, typically within the non-translated leader.

In some embodiments, a construct for expression of the heterologous nucleic acid sequence of interest also includes a regulator such as a nuclear localization signal (Kalderon et al., 1984, Cell 39:499; Lassner et al., 1991, Plant Molecular Biology 17:229), a plant translational consensus sequence (Joshi, 1987, Nucleic Acids Research 15:6643), an intron (Luehrsen and Walbot, 1991, Mol. Gen. Genet. 225:81), and the like, operably linked to the nucleic acid sequence encoding an heterologous gene.

In preparing the construct comprising the nucleic acid sequence encoding a heterologous gene, or encoding a sequence designed to decrease heterologous gene expression, various DNA fragments can be manipulated so as to provide for the DNA sequences in the desired orientation (e.g., sense or antisense) and, as appropriate, in the desired reading frame. For example, adapters or linkers can be employed to join the DNA fragments, or other manipulations can be used to provide for convenient restriction sites, removal of superfluous DNA, removal of restriction sites, and the like. For this purpose, in vitro mutagenesis, primer repair, restriction, annealing, resection, ligation, and the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, 1982, Gene 19: 259; Bevan et al., 1983, Nature 304:184, all of which are incorporated herein by reference), the bar gene which confers resistance to the herbicide phosphinothricin (White et al., 1990. Nucl Acids Res. 18:1062; Spencer et al., 1990. Theor. Appl. Genet. 79:625, all of which are incorporated herein by reference in their entireties), the hph gene which confers resistance to the antibiotic hygromycin (Blochlinger and Diggelmann, 1984, Mol. Cell. Biol. 4:2929, incorporated herein by reference in its entirety), and the dhfr gene that confers resistance to methotrexate (Bourouis et al., 1983, EMBO J., 2:1099, incorporated herein by reference in its entirety).

In some embodiments, the Ti (T-DNA) plasmid vector is adapted for use in an *Agrobacterium* mediated transfection process such as in U.S. Pat. No. 6,369,298 (*sorghum*), and U.S. Pat. Nos. 5,981,839, 6,051,757, 5,981,840, 5,824,877 and 4,940,838 all of which are incorporated by reference herein in their entireties. Construction of recombinant Ti and Ri plasmids in general follows methods typically used with more common vectors, such as pBR322. Additional use can be made of accessory genetic elements sometimes found with the native plasmids and sometimes constructed from foreign sequences. These may include, but are not limited to, structural genes for antibiotic resistance as selection genes.

There are two systems of recombinant Ti and Ri plasmid vector systems now in use. The first system is called the "co-integrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Application Nos. WO 84/02913, 02919 and 02920; Herrera-Estrella, 1983, Nature 303:209-213; Fraley et al., 1983, Proc. Natl. Acad. Sci, USA 80:4803-4807; Horsch et al., 1984, Science 223:496-498; and DeBlock et al., 1984, EMBO J. 3:1681-1689, all of which are herein incorporated by reference in their entireties.

The second system is called the "binary" system in which two plasmids are used and the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In some embodiments, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967 herein incorporated by reference in its entirety). One of skill in the art knows that homologous recombination may be achieved using targeting vectors that contain sequences that are homologous to any part of the targeted plant gene, whether belonging to the regulatory elements of the gene or the coding regions of the gene.

Homologous recombination may be achieved at any region of a plant gene so long as the nucleic acid sequence of regions flanking the site to be targeted is known. *Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

In some embodiments, the nucleic acids as disclosed herein are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or another promoter. Methods for the construction and use of such viruses are described in U.S. Pat. Nos. 5,846,795; 5,500,360; 5,173,410; 5,965,794; 5,977,438; and 5,866,785, all of which are incorporated herein by reference in their entireties.

In some embodiments, a heterologous nucleic acid sequence of interest comprising a mutant ALS transgene as found in the germplasm KSU 06MN8419 deposited under ATCC No: PTA-7999 is introduced directly into a plant. In some embodiments, the mutant ALS transgene is at least 70% homologous, at least 80% homologous, at least 85% homologous, at least 90% homologous, at least 95% homologous, at least 97% homologous, or at least 99% homologous to the ALS gene as found in the germplasm KSU 06MN8419. In some embodiments, the mutant ALS transgene that is at least 70% homologous, at least 80% homologous, at least 85% homologous, at least 90% homologous, at least 95% homologous, at least 97% homologous, or at least 99% homologous to the ALS herbicide resistant gene as found in the germplasm KSU 06MN8419 comprises one or more of the amino acid substitutions $Val_{531}Ile$ and $Trp_{545}Leu$. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278, herein incorporated by reference).

Once a nucleic acid sequence encoding the heterologous gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method depends on the type of plant targeted for transformation. In some embodiments, the vector is maintained episomally. In some embodiments, the vector is integrated into the genome. In some embodiments, direct transformation in the plastid genome is used to introduce the vector into the plant cell (for example, see U.S. Pat. Nos. 5,451,513; 5,545,817; 5,545,818; PCT application WO 95/16783 all of which are incorporated herein by reference in their entireties).

The basic technique for chloroplast transformation involves introducing regions of cloned plastid DNA flanking a selectable marker together with the nucleic acid encoding the sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., 1990, Proc. Natl. Acad. Sci., 87:8526; Staub and Maliga, 1992, Plant Cell, 4:39, all of which are incorporated herein by reference). The presence of cloning sites between these markers allows creation of a plastid targeting vector introduction of foreign DNA molecules (Staub and Maliga, 1993, EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, 1993, Proc. Natl. Acad. Sci., 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of RNAs encoded by the DNA molecule.

In one embodiment, vectors useful in the practice of the present invention are microinjected directly into plant cells (Crossway, 1985, Mol. Gen. Genet., 202:179). In some embodiments, the vector is transferred into the plant cell by using polyethylene glycol (Krens et al., 1982, Nature, 296: 72; Crossway et al., 1986, BioTechniques, 4:320); fusion of protoplasts with other entities such as minicells, cells, lysosomes or other fusible lipid-surfaced bodies (Fraley et al., 1982, Proc. Natl. Acad. Sci., USA, 79:1859); and protoplast transformation (EP 0 292 435); direct gene transfer (Paszkowski et al., 1984, EMBO J., 3:2717; Hayashimoto et al., 1990, Plant Physiol. 93:857).

In some embodiments, the vector may also be introduced into the plant cells by electroporation. (Fromm, et al., 1985, Proc. Natl. Acad. Sci. USA 82:5824; Riggs et al., 1986, Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus. In addition to direct transformation, in some embodiments, the vectors comprising a nucleic acid sequence encoding a heterologous gene are transferred using *Agrobacterium*-mediated transformation (Hinchee et al., 1988, Biotechnology, 6:915; Ishida et al., 1996, Nature Biotechnology 14:745, all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introduced into appropriate plant cells, by means of the Ti plasmid of *Agrobacterium tumefaciens* (previously described). The Ti plasmid is transmitted to plant cells on infection by *Agrobacterium tumefaciens*, and is stably integrated into the plant genome (Schell, 1987, Science, 237: 1176). Species that are susceptible to infection by *Agrobacterium* may be transformed in vitro. Transformation methods for producing transgenic *sorghum* plants using *Agrobacterium*-mediated transformation are provided in U.S. Pat. No. 6,369,298.

In some embodiments, the vector is introduced through ballistic particle acceleration (U.S. Pat. No. 4,945,050; Casas et al., 1993, Proc. Natl. Acad. Sci. USA 90:11212, all references are incorporated herein in their entireties).

In some embodiments, after selecting for transformed plant material that can express a heterologous gene encoding a heterologous protein or variant thereof, whole plants are regenerated. Plant regeneration from cultured protoplasts is described in Evans et al., Handbook of Plant Cell Cultures, Vol. 1: (MacMillan Publishing Co. New York, (1983); Vasil I. R. (ed.), Cell Culture and Somatic Cell Genetics of Plants, Acad. Press, Orlando, Vol. I, (1984) and Vol. III, (1986), incorporated herein by reference in their entireties. It is known that many plants can be regenerated from cultured cells or tissues including, but not limited to, all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins Shoots and roots normally develop simultaneously. Efficient regeneration will depend on the medium, on the genotype, and on the history of the culture. The reproducibility of regeneration depends on the control of these variables.

EXAMPLES

Example 1—Herbicide Resistance in *Sorghum* Genotype

Seeds of the wild *sorghum* genotype shown to exhibit an ALS resistant phenotype, designated "Tailwind", and an herbicide susceptible *sorghum* genotype designated 90SN7 were planted in 12 liter pots in a greenhouse. Several of each type of plant were sprayed with either 1) Lightning Herbicide (a combination of Imazethapyr and Imazapyr) at the rate of 2.56 oz acre$^{-1}$ (a 2× herbicide rate), 2) Steadfast® Herbicide (DuPont™; a combination of Nicosulfuron and Rimsulfuron) at a rate of 1.50 oz acre$^{-1}$ (a 2× herbicide), or 3) a combination of Lightning Herbicide at 2.56 oz acre$^{-1}$ rate and Steadfast® Herbicide at 1.50 oz acre$^{-1}$ rate. For each treatment, the Tailwind plants showed essentially no damage after 12 days of herbicide application, while the 90SN7 plants were dead, demonstrating that Tailwind had cross-resistance to IMI (Lightening Herbicide) and SU (Steadfast® Herbicide) classes of ALS inhibiting herbicides.

Example 2—Crosses of Tailwind with Elite *Sorghum* Parental Lines

Tailwind was crossed with various elite parents including Tx430 and Wheatland. F2 populations derived from crosses with these parents were evaluated by segregation analysis to determine the number of genes involved in the expression of tolerance. Plant populations were grown in a greenhouse and were sprayed with 1× and 3× rates of Accent® Herbicide (DuPont™; Nicosulfuron), Option® Herbicide (BayerCropScience; Foramsulfuron), and Steadfast® Herbicide. Population counts of live/dead plants allowed genetic analyses.

Segregation analysis indicated a single major, partially dominant gene in the population derived from Tx430 for each herbicide treatment. Similar analyses of populations derived from crosses with Wheatland indicated a single major, partially dominant gene as well as potentially two or three modifier genes that influenced the relative expression of the tolerance trait.

Plant breeding efforts were initiated by backcrossing the tolerance trait into commercially important elite *sorghum* pollinator parents including Tx430, Tx2737, Tx2783, 00MN7645, and HP162 as well as commercially important elite *sorghum* seed parents including Wheatland, Tx3042, OK11, QL41 and Tx643, with selection for herbicide tolerance in each generation. The resultant seed from the cross of Tailwind with Tx2783 (BC$_2$F$_3$:F$_4$) was deposited at ATCC for public access.

Example 3—Gene Sequencing for ALS Resistance Gene

Gene sequencing efforts were initiated to determine if a target sight mutation existed for the herbicide tolerance phenotype. A sequence search performed using the National Institute of Health's Basic Local Alignment Search Tool (BLAST) in The Institute for Genomic Research (TIGR) Plant Transcript Assemblies database identified a Transcript Assembly representing a *sorghum* ALS gene (TA3960_4558; SEQ ID NO: 1). Amplification primers for polymerase chain reaction (PCR) were designed, F4r-CA-CATCACCCTTGTACCAGCTC (SEQ ID NO: 3) and B5-GATTGTGCACATTGATATTGATCC (SEQ ID NO: 4), to amplify regions of the *sorghum* gene analogous to regions of the *Arabidopsis thaliana* AHAS gene thought to influence the expression of ALS-herbicide tolerance (*A. thaliana*: Ala$_{122}$, Pro$_{197}$, Ala$_{205}$, Trp$_{574}$, and Ser$_{653}$; Tan et al., 2005).

Polymerase chain reaction amplification primers were successfully used to amplify the region of the gene in herbicide resistant (S1-1, S1-2 and S1-3) and susceptible (Tx623 and Tx430) *sorghum* genotypes using the following thermocycling conditions: denaturation at 94° C. for 60 seconds, annealing at 62° C. for 45 seconds, and extension at 72° C. for 45 seconds. The PCR amplification products were purified using the QIAquick PCR Purification Kit (QIAGEN) and sequenced at the Kansas State University sequencing facility. The deduced amino acid sequence (SEQ ID NO: 2) shows mutations at Val$_{531}$Ile (GTC to ATC), corresponding to *A. thaliana* Val$_{560}$Ile, and Trp$_{545}$Leu (TGG to TTG), corresponding to *A. thaliana* Trp$_{574}$Leu, in herbicide resistant genotypes (FIG. 1).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A seed of a *sorghum* hybrid, wherein representative seeds have been deposited under ATCC No. PTA-7999, wherein said seed comprises a polynucleotide comprising the nucleotide sequence represented by SEQ ID NO: 1, provided that said nucleotide sequence comprises a guanine to adenine nucleic acid substitution at position 1641 and a guanine to thymine nucleic acid substitution at position 1684.

2. A *sorghum* plant grown from the seed of claim 1.

3. Plant tissue obtained from the *sorghum* plant of claim 2.

4. Grain obtained from the *sorghum* plant of claim 2, wherein said grain comprises the polynucleotide comprising the nucleotide sequence represented by SEQ ID NO: 1, provided that said nucleotide sequence comprises a guanine to adenine nucleic acid substitution at position 1641 and a guanine to thymine nucleic acid substitution at position 1684.

5. The seed of claim 1, wherein said seed is coated with one or more acetoacetate synthase herbicides.

6. The seed of claim 5, wherein said one or more acetoacetate synthase herbicides are selected from the group consisting of sulfonylureas, imidazolinones, triazolopyrimidines, and pyrimidinylthiobenzoates.

7. The seed of claim 6, wherein the sulfonylurea herbicide is selected from the group consisting of nicosulfuron, rimsulfuron, and metsulfuron-methyl.

* * * * *

SEQUENCE LISTING

<160> NUMBER OF SEQ ID NOS: 12

<210> SEQ ID NO 1
<211> LENGTH: 2274
<212> TYPE: DNA
<213> ORGANISM: Sorghum bicolor

<400> SEQUENCE: 1

| | | | | | | |
|---|---|---|---|---|---|---|
| gtgccccgc | cccaaaccct | cgcgccgcct | ccgagacagc | cgccgcaacc | atggccacca | 60 |
| ccgccgccgc | cgctgccgcc | gcgctagccg | gcgccactac | cgctgcgccc | aaggcgaggc | 120 |
| gccgggcgca | cctcctggcc | gcacggcgcg | ccctcgccgc | gcccatcagg | tgctcagcgg | 180 |
| cgccacccgc | cacgctgacg | gtgacggctc | ccccggccac | cccgctccgg | ccgtggggcc | 240 |
| ccaccgatcc | ccgcaagggc | gccgacatcc | tcgtcgaggc | tcttgagcgc | tgcggcgtcc | 300 |
| gcgacgtctt | cgcctacccc | ggcggcgcgt | ccatggagat | ccaccaggca | ctcacccgtt | 360 |
| cccccgtcat | cgccaaccac | ctcttccgcc | acgagcaagg | ggaggccttc | gccgcctctg | 420 |
| gcttcgcgcg | ctcctcgggc | cgcgtcggcg | tctgcgtcgc | cacctccggc | cccggcgcca | 480 |
| ccaacctagt | ctccgcgctc | gccgacgcgc | tgctcgactc | cgtccccatg | gtcgccatca | 540 |
| cgggacaggt | tccgcggcgc | atgattggca | ccgacgcctt | ccaggagacg | cccatcgtcg | 600 |
| aggtcacccg | ctccatcacc | aaacataact | acctggtcct | cgacgtcgac | gacatccccc | 660 |
| gcgtcgtgca | ggaggctttc | ttcctcgcct | cctccggtcg | cccgggaccg | gtgcttgtcg | 720 |
| acatccccaa | ggacatccag | cagcagatgg | ccgtgccggt | ctgggacacg | cccatgagtc | 780 |
| tgcctgggta | cattgcgcgc | cttcccaagc | ctcctgcgac | tgaattgctt | gagcaggtgc | 840 |
| tgcgtcttgt | tggtgaatca | aggcgccctg | ttctttatgt | tggtggtggc | tgcgcagcat | 900 |
| ctggcgagga | gttgcgccgc | tttgtggaga | tgactggaat | cccagtcaca | actactctta | 960 |
| tgggccttgg | caatttccct | ggcgacgacc | cactgtctct | cgcatgcttg | gtatgcatg | 1020 |
| gcacggtgta | tgcaaattat | gcagtggata | aggcggatct | gttgcttgca | tttggtgtgc | 1080 |
| ggtttgatga | tcgtgtgaca | gggaagattg | aggcttttgc | aagcagggct | aagattgtgc | 1140 |
| acattgatat | tgatcccgct | gagattggca | agaacaagca | gccacatgtg | tccatctgtg | 1200 |
| cagacgttaa | gcttgctttg | cagggcatga | atgctcttct | ggaaggaagc | acatcaaaga | 1260 |
| agagctttga | ctttggctca | tggcaagctg | agttggatca | gcagaagaga | gagttccccc | 1320 |
| ttgggtataa | aactttttgat | gacgagatcc | agccacaata | tgctattcag | gttcttgatg | 1380 |
| agctgacaaa | aggggaggcc | atcattgcca | caggtgttgg | gcagcaccag | atgtgggcgg | 1440 |
| cacagtacta | cacttacaag | cggccaaggc | agtggttgtc | ttcagctggt | cttgggcta | 1500 |
| tgggatttgg | tttgccggct | gctgctggcg | ctgctgtggc | caacccaggt | atcactgttg | 1560 |
| ttgacatcga | cggagatggt | agcttcctca | tgaacattca | ggagctagct | atgatccgaa | 1620 |
| ttgagaacct | cccagtgaag | gtcttttgtg | ctaaacaacca | gcacctgggg | atggtggtgc | 1680 |
| agtgggagga | caggttctat | aaggccaata | gagcacacac | atacttggga | aacccagaga | 1740 |
| atgaaagtga | gatatatcca | gatttcgtga | caattgccaa | agggttcaac | attccagcag | 1800 |
| tccgtgtgac | aaagaagagc | gaagtccatg | cagcaatcaa | gaagatgctt | gagactccag | 1860 |
| ggccatacct | cttggatata | atcgtcccgc | caccaggagca | tgtgttgcct | atgatcccta | 1920 |
| gtggtggggc | tttcaaggat | atgatcctgg | atggtgatgg | caggactgtg | tattgatcta | 1980 |
| aatttcagca | tgcacatctc | cctgcctttc | tttgacatgc | atatgagctg | gtacaagggt | 2040 |
| gatgtgttat | ttatgtgatg | ttctcctgtg | ttctatctt | ttgtaagccg | tcagctatct | 2100 |

```
atagtgtgct tgtttgatgt actctgttat ggtaatctta agtagtttcc taccttgtag      2160
tggtgtagtc tgttgtttcg tgctggcata tctgtcatca gaggtcatgt aagtgccttt      2220
tgctacagat aaataaggaa ataagcattg ctatgcagtg gttctgtacg cctc            2274
```

<210> SEQ ID NO 2
<211> LENGTH: 641
<212> TYPE: PRT
<213> ORGANISM: Sorghum bicolor

<400> SEQUENCE: 2

```
Met Ala Thr Thr Ala Ala Ala Ala Ala Ala Leu Ala Gly Ala Thr
1               5                   10                  15

Thr Ala Ala Pro Lys Ala Arg Arg Ala His Leu Leu Ala Ala Arg
            20                  25                  30

Arg Ala Leu Ala Ala Pro Ile Arg Cys Ser Ala Ala Pro Ala Thr
        35                  40                  45

Leu Thr Val Thr Ala Pro Pro Ala Thr Pro Leu Arg Pro Trp Gly Pro
    50                  55                  60

Thr Asp Pro Arg Lys Gly Ala Asp Ile Leu Val Glu Ala Leu Glu Arg
65                  70                  75                  80

Cys Gly Val Arg Asp Val Phe Ala Tyr Pro Gly Ala Ser Met Glu
                85                  90                  95

Ile His Gln Ala Leu Thr Arg Ser Pro Val Ile Ala Asn His Leu Phe
            100                 105                 110

Arg His Glu Gln Gly Glu Ala Phe Ala Ala Ser Gly Phe Ala Arg Ser
        115                 120                 125

Ser Gly Arg Val Gly Val Cys Val Ala Thr Ser Gly Pro Gly Ala Thr
    130                 135                 140

Asn Leu Val Ser Ala Leu Ala Asp Ala Leu Leu Asp Ser Val Pro Met
145                 150                 155                 160

Val Ala Ile Thr Gly Gln Val Pro Arg Arg Met Ile Gly Thr Asp Ala
                165                 170                 175

Phe Gln Glu Thr Pro Ile Val Glu Val Thr Arg Ser Ile Thr Lys His
            180                 185                 190

Asn Tyr Leu Val Leu Asp Val Asp Asp Ile Pro Arg Val Val Gln Glu
        195                 200                 205

Ala Phe Phe Leu Ala Ser Ser Gly Arg Pro Gly Pro Val Leu Val Asp
    210                 215                 220

Ile Pro Lys Asp Ile Gln Gln Gln Met Ala Val Pro Val Trp Asp Thr
225                 230                 235                 240

Pro Met Ser Leu Pro Gly Tyr Ile Ala Arg Leu Pro Lys Pro Pro Ala
                245                 250                 255

Thr Glu Leu Leu Glu Gln Val Leu Arg Leu Val Gly Glu Ser Arg Arg
            260                 265                 270

Pro Val Leu Tyr Val Gly Gly Gly Cys Ala Ala Ser Gly Glu Glu Leu
        275                 280                 285

Arg Arg Phe Val Glu Met Thr Gly Ile Pro Val Thr Thr Thr Leu Met
    290                 295                 300

Gly Leu Gly Asn Phe Pro Gly Asp Asp Pro Leu Ser Leu Arg Met Leu
305                 310                 315                 320

Gly Met His Gly Thr Val Tyr Ala Asn Tyr Ala Val Asp Lys Ala Asp
                325                 330                 335

Leu Leu Leu Ala Phe Gly Val Arg Phe Asp Asp Arg Val Thr Gly Lys
```

```
            340                 345                 350
Ile Glu Ala Phe Ala Ser Arg Ala Lys Ile Val His Ile Asp Ile Asp
            355                 360                 365

Pro Ala Glu Ile Gly Lys Asn Lys Gln Pro His Val Ser Ile Cys Ala
370                 375                 380

Asp Val Lys Leu Ala Leu Gln Gly Met Asn Ala Leu Leu Glu Gly Ser
385                 390                 395                 400

Thr Ser Lys Lys Ser Phe Asp Phe Gly Ser Trp Gln Ala Glu Leu Asp
                405                 410                 415

Gln Gln Lys Arg Glu Phe Pro Leu Gly Tyr Lys Thr Phe Asp Asp Glu
            420                 425                 430

Ile Gln Pro Gln Tyr Ala Ile Gln Val Leu Asp Glu Leu Thr Lys Gly
            435                 440                 445

Glu Ala Ile Ile Ala Thr Gly Val Gly Gln His Gln Met Trp Ala Ala
            450                 455                 460

Gln Tyr Tyr Thr Tyr Lys Arg Pro Arg Gln Trp Leu Ser Ser Ala Gly
465                 470                 475                 480

Leu Gly Ala Met Gly Phe Gly Leu Pro Ala Ala Gly Ala Ala Val
                485                 490                 495

Ala Asn Pro Gly Ile Thr Val Val Asp Ile Asp Gly Asp Gly Ser Phe
                500                 505                 510

Leu Met Asn Ile Gln Glu Leu Ala Met Ile Arg Ile Glu Asn Leu Pro
            515                 520                 525

Val Lys Val Phe Val Leu Asn Asn Gln His Leu Gly Met Val Val Gln
            530                 535                 540

Trp Glu Asp Arg Phe Tyr Lys Ala Asn Arg Ala His Thr Tyr Leu Gly
545                 550                 555                 560

Asn Pro Glu Asn Glu Ser Glu Ile Tyr Pro Asp Phe Val Thr Ile Ala
                565                 570                 575

Lys Gly Phe Asn Ile Pro Ala Val Arg Val Thr Lys Lys Ser Glu Val
                580                 585                 590

His Ala Ala Ile Lys Lys Met Leu Glu Thr Pro Gly Pro Tyr Leu Leu
            595                 600                 605

Asp Ile Ile Val Pro His Gln Glu His Val Leu Pro Met Ile Pro Ser
            610                 615                 620

Gly Gly Ala Phe Lys Asp Met Ile Leu Asp Gly Asp Gly Arg Thr Val
625                 630                 635                 640

Tyr
```

<210> SEQ ID NO 3
<211> LENGTH: 22
<212> TYPE: DNA
<213> ORGANISM: Artificial Sequence
<220> FEATURE:
<223> OTHER INFORMATION: synthetic

<400> SEQUENCE: 3
cacatcaccc ttgtaccagc tc                                            22

<210> SEQ ID NO 4
<211> LENGTH: 24
<212> TYPE: DNA
<213> ORGANISM: Artificial Sequence
<220> FEATURE:
<223> OTHER INFORMATION: synthetic

<400> SEQUENCE: 4

```
gattgtgcac attgatattg atcc                                             24

<210> SEQ ID NO 5
<211> LENGTH: 83
<212> TYPE: DNA
<213> ORGANISM: Sorghum bicolor

<400> SEQUENCE: 5
cccagtgaag gtctttgtgc taaacaacca gcacctgggg atggtggtgc agtgggagga     60
caggttctat aaggccaata gag                                             83

<210> SEQ ID NO 6
<211> LENGTH: 83
<212> TYPE: DNA
<213> ORGANISM: Sorghum bicolor

<400> SEQUENCE: 6
cccagtgaag gtctttgtgc taaacaacca gcacctgggg atggtggtgc agtgggagga     60
caggttctat aaggccaata gag                                             83

<210> SEQ ID NO 7
<211> LENGTH: 83
<212> TYPE: DNA
<213> ORGANISM: Sorghum bicolor

<400> SEQUENCE: 7
cccagtgaag gtctttgtgc taaacaacca gcacctgggg atggtggtgc agtgggagga     60
caggttctat aaggccaata gag                                             83

<210> SEQ ID NO 8
<211> LENGTH: 83
<212> TYPE: DNA
<213> ORGANISM: Sorghum bicolor

<400> SEQUENCE: 8
cccagtgaag gtctttgtgc taaacaacca gcacctgggg atggtggtgc agtgggagga     60
caggttctat aaggccaata gag                                             83

<210> SEQ ID NO 9
<211> LENGTH: 83
<212> TYPE: DNA
<213> ORGANISM: Sorghum bicolor

<400> SEQUENCE: 9
cccagtgaag atctttgtgc taaacaacca gcacctgggg atggtggtgc agttggagga     60
caggttctat aaggccaata gag                                             83

<210> SEQ ID NO 10
<211> LENGTH: 83
<212> TYPE: DNA
<213> ORGANISM: Sorghum bicolor

<400> SEQUENCE: 10
cccagtgaag atctttgtgc taaacaacca gcacctgggg atggtggtgc agttggagga     60
caggttctat aaggccaata gag                                             83

<210> SEQ ID NO 11
<211> LENGTH: 83
<212> TYPE: DNA
```

```
<213> ORGANISM: Sorghum bicolor

<400> SEQUENCE: 11
cccagtgaag atctttgtgc taaacaacca gcacctgggg atggtggtgc agttggagga        60
caggttctat aaggccaata gag                                                83

<210> SEQ ID NO 12
<211> LENGTH: 83
<212> TYPE: DNA
<213> ORGANISM: Sorghum bicolor

<400> SEQUENCE: 12
cccagtgaag atctttgtgc taaacaacca gcacctgggg atggtggtgc agttggagga        60
caggttctat aaggccaata gag                                                83
```